United States Patent [19]

Golovin

[11] Patent Number: 5,262,253
[45] Date of Patent: Nov. 16, 1993

[54] SOLID ELECTROLYTES DERIVED BY POLYMERIZATION OF VINYL SULFONATE POLYALKYLENE OXIDES

[75] Inventor: Milton N. Golovin, San Jose, Calif.

[73] Assignee: Valence Technology, Inc., San Jose, Calif.

[21] Appl. No.: 918,438

[22] Filed: Jul. 22, 1992

[51] Int. Cl.$^5$ .................. H01M 10/40; C08G 75/18; C07C 303/00

[52] U.S. Cl. .................. 429/192; 528/391; 528/421; 558/46; 558/51; 558/55

[58] Field of Search .................. 429/192; 521/34; 528/391, 421; 558/46, 51, 55

[56] References Cited

U.S. PATENT DOCUMENTS

| | | | |
|---|---|---|---|
| 3,335,163 | 8/1967 | Tesoro et al. | 558/51 X |
| 4,079,084 | 3/1978 | Houghton | 558/46 X |
| 4,737,422 | 4/1988 | Knight et al. | 429/192 |
| 4,830,939 | 5/1989 | Lee et al. | 429/192 |
| 4,908,283 | 3/1990 | Takahashi et al. | 429/192 |
| 4,925,751 | 5/1990 | Shackle et al. | 429/191 |

FOREIGN PATENT DOCUMENTS 2044837  4/1972  Fed. Rep. of Germany ........ 558/51

OTHER PUBLICATIONS

Cram & Hammond, "Organic Chemistry", p 441 (1959).
Schwartz, J. Org. Chem., vol. 33, No. 7, pp. 2895-2902 (1968).

Primary Examiner—Stephen Kalafut
Attorney, Agent, or Firm—Gerald F. Swiss

[57] ABSTRACT

This invention is directed to solid electrolytes containing a solid polymeric matrix derived from vinyl sulfonate polyalkylene oxides.

24 Claims, No Drawings

SOLID ELECTROLYTES DERIVED BY POLYMERIZATION OF VINYL SULFONATE POLYALKYLENE OXIDES

BACKGROUND OF THE INVENTION

1. Field of the Invention

This invention is directed to novel vinyl sulfonate polyalkylene oxides as well as to solid electrolytes derived by polymerization of such vinyl sulfonate polyalkylene oxides.

2. State of the Art

Electrolytic cells containing an anode, a cathode and a solid, solvent-containing electrolyte are known in the art and are usually referred to as "solid batteries". These cells offer a number of advantages over electrolytic cells containing a liquid electrolyte (i.e., "liquid batteries") including improved safety features.

The solid, solvent-containing electrolyte employed in such solid batteries contains either an inorganic matrix or an organic polymeric matrix as well as a suitable inorganic ion salt. Because of their expense and difficulty in forming into a variety of shapes, inorganic non-polymeric matrices are, however, not preferred and the art typically employs a solid electrolyte containing an organic or inorganic polymeric matrix.

Suitable organic polymeric matrices are well known in the art and are typically organic homopolymers obtained by polymerization of a suitable organic monomer as described, for example, in U.S. Pat. No. 4,908,283 or copolymers obtained by polymerization of a mixture of organic monomers. Suitable organic monomers include, by way of ethylene oxide, propylene oxide, ethyleneimine, epichlorohydrin, ethylene succinate, and an acryloyl-derivatized polyalkylene oxide containing an acryloyl group of the formula $CH_2=CR'C(O)O-$ where R' is hydrogen or lower alkyl of from 1–6 carbon atoms.

One problem associated with the polymerization of certain organic monomers is that rather strong conditions are required to effect the desired degree of polymerization. The strong conditions used, in turn, can have an adverse effect on the partially manufactured battery components treated under these conditions. Accordingly, the art has been searching for organic monomers which are readily polymerized and which, when polymerized, form suitable solid polymeric matrices for use in preparing solid electrolytes.

Additionally, suitable organic monomers preferably contain at least one hetero atom capable of forming donor acceptor bonds with inorganic cations (e.g., alkali ions). When polymerized, these compounds form a polymer suitable for use an ionically conductive matrix in a solid electrolyte.

SUMMARY OF THE INVENTION

The present invention is directed, in part, to the discovery of novel polyalkylene oxide vinyl sulfonate (i.e., monomers) which are readily polymerized and, when polymerized, the resulting polymer forms an ionically conductive matrix. The organic monomers of this invention are represented by Formula I:

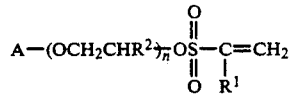

where $R^1$ is selected from the group consisting of hydrogen and alkyl of from 1 to 6 carbon atoms; $R^2$ is selected from the group consisting of hydrogen and an alkyl group of from 1 to 3 carbon atoms; A is selected from the group consisting of a hydrocarbyl group of from 1 to 30 carbon atoms and a compatible ethylenically unsaturated moiety of from 2 to 6 carbon atoms; and n is an integer from about 2 to 50.

When polymerized, these compounds form a polymer suitable for use as an ionically conductive matrix in a solid electrolyte. Accordingly, in another of its composition aspects, this invention is directed to a single phase, solid, solvent-containing electrolyte which comprises:
- a solid polymeric matrix;
- an inorganic ion salt; and
- a solvent;

wherein said solid polymeric matrix is obtained by polymerizing an organic monomer represented by Formula I:

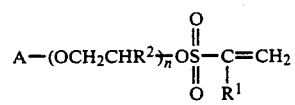

where $R^1$ is selected from the group consisting of hydrogen and alkyl of from 1 to 6 carbon atoms; $R^2$ is selected from the group consisting of hydrogen and an alkyl group of from 1 to 3 carbon atoms; A is selected from the group consisting of a hydrocarbyl group of from 1 to 30 carbon atoms and a compatible ethylenically unsaturated moiety of from 2 to 6 carbon atoms; and n is an integer from about 2 to 50.

In another of its composition aspects, the present invention is directed to an electrolytic cell which comprises:
- an anode comprising a compatible anodic material;
- a cathode comprising a compatible cathodic material; and
- interposed therebetween a single phase, solid, solvent-containing electrolyte which comprises:
  - a solid polymeric matrix;
  - an inorganic ion salt; and
  - a solvent wherein said solid polymeric matrix is obtained by polymerizing an organic monomer represented by Formula I:

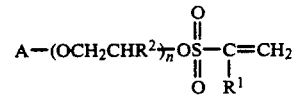

where $R^1$ is selected from the group consisting of hydrogen and alkyl of from 1 to 6 carbon atoms; $R^2$ is selected from the group consisting of hydrogen and an alkyl group of from 1 to 3 carbon atoms; A is selected from the group consisting of a hydrocarbyl group of from 1 to 30 carbon atoms and a compatible ethylenically unsaturated moiety of from 2 to 6 carbon atoms; and n is an integer from about 2 to 50.

Preferably, R is hydrogen or methyl and most preferably R is hydrogen.

Preferably, $R^1$ is hydrogen or methyl and more preferably, $R^1$ is hydrogen.

Preferably, A is represented by the group:

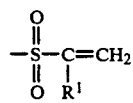

where $R^1$ is as defined above; and more preferably where $R^1$ is hydrogen.

DETAILED DESCRIPTION OF THE PREFERRED EMBODIMENTS

As noted above, this invention is directed to solid, solvent-containing electrolytes which, employ a specific solid, polymeric, ion-conducting matrix. However, prior to describing this invention is further detail, the following terms will first be defined.

Definitions

As used herein, the following terms have the following meanings.

The term "solid polymeric matrix" refers to an ion-conductive matrix formed by polymerizing an organic monomer containing at least one hetero atom capable of forming donor acceptor bonds with inorganic cations derived from inorganic ion salts under conditions such that the resulting polymer is useful in preparing solid electrolytes. Solid polymeric matrices are well known in the art and are described, for example, in U.S. Pat. No. 4,908,283 and in U.S. Pat. No. 4,925,751 both of which are incorporated herein by reference in their entirety.

The term "inorganic ion salt" refers to any inorganic salt which is suitable for use in a solid electrolyte. The particular inorganic ion salt employed is not critical and examples of suitable inorganic ion salts include, by way of example, $LiClO_4$, $LiI$, $LiSCN$, $LiBF_4$, $LiAsF_6$, $LiCF_3SO_3$, $LiPF_6$, $NaI$, $NaSCN$, $KI$, $CsSCN$, $AgNO_3$, $CuCl_2$, $Mg(ClO_4)_2$ and the like. The inorganic ion salt preferably contains at least one atom selected from the group consisting of Li, Na, K, Cs, Ag, Cu and Mg.

The term "electrolyte solvent" refers to the solvent (i.e., plasticizer) added to the electrolyte and/or the cathode for the purpose of solubilizing the inorganic ion salt. The solvent can be any low volatile aprotic polar solvent. Preferably, these materials are characterized by a boiling point greater than about 80° C. In this regard, low volatility for the electrolyte solvent simplifies manufacture of the electrolyte/batteries and improves their self-life.

If the solid polymeric matrix is formed by radiation polymerization of the monomer of Formula I, then the solvent should be radiation inert at least up to the levels of radiation employed. If the solid polymeric matrix is formed by thermal polymerization, the solvent should be thermally inert at least up to the temperatures of thermal polymerization. Additionally, the solvent should not scavenge free radicals.

Representative examples of suitable solvents include propylene carbonate, ethylene carbonate, Y-butyrolactone, tetrahydrofuran, glyme (dimethoxyethane), diglyme, triglyme, tetraglyme, dimethylsulfoxide, dioxolane, sulfolane and the like. A particularly preferred solvent is a mixture of an organic carbonate and triglyme as disclosed in U.S. patent application Ser. No. 07/918,509 which application is incorporated herein by reference in its entirety.

The term "cured" or "cured product" refers to the treatment of the monomer of Formula I above (or partial polymer thereof) under polymerization conditions (including cross-linking) so as to form a solid polymeric matrix. Suitable polymerization conditions are well known in the art and include by way of example, heating the monomer, irradiating the monomer with UV light, electron beams, etc. Because the resulting solid polymeric matrix (i.e., cured product) contains repeating units having at least one oxygen (hetero) atom, the matrix is capable of forming donor acceptor bonds with inorganic cations (alkali ions) and is, accordingly, ion-conducting.

The monomer of Formula I (or partial polymer thereof) can be cured (or further cured) prior to or after addition of the inorganic ion salt and the electrolyte solvent. For example, a composition comprising requisite amounts of the monomer, the inorganic ion salt and the electrolyte solvent can be applied to a suitable substrate (e.g., the surface of the cathode) and then cured. Alternatively, the monomer of Formula I can be first cured and then dissolved into a suitable volatile solvent. Requisite amounts of the inorganic ion salt and electrolyte solvent can then be added to the solution containing the cured monomer of Formula I (i.e., the solid polymeric matrix). The mixture is then placed on a substrate and removal of the volatile solvent results in formation of a solid electrolyte. In either case, the resulting solid electrolyte is a homogeneous, single phase product which is maintained upon curing, and does not readily separate upon cooling to temperatures below room temperature. Accordingly, the solid electrolyte of this invention does not include a separator as is typical of liquid electrolytes.

The term "hydrocarbyl" refers to organic radicals composed of carbon and hydrogen which may be aliphatic, alicyclic, aromatic or combinations thereof, e.g., aralkyl. Exemplary hydrocarbyl groups include alkyls such as methyl, ethyl, propyl, butyl, isobutyl, pentyl, hexyl, octyl, and the like, alkenyls such as propenyl, isobutenyl, hexenyl, octenyl, and the like, aromatics such as phenyl, alkylphenyls including 4-methylphenyl, 4-ethylphenyl, and the like, alkoxy such ethoxyethyl, propoxyethyl, and the like.

The term "a compatible ethylenically unsaturated moiety of from 2 to about 6 carbon atoms" refers to unsaturated moieties attached to the polyalkylene oxide chain through a suitable linking group and which either do not interfere with or which participate in the polymerization reactions to form a solid polymeric matrix. Suitable compatible ethylenically unsaturated moieties include, by way of example, $CH_2=CR'C(O)-$ where $R'$ is hydrogen or alkyl of from 1 to 3 carbon atoms; a substituent of the formula

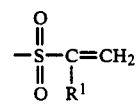

where $R^1$ is defined above; $CH_2=CH(CH_2)_p-$ where p is an integer from 1 to 5; and the like.

The ethylenically unsaturated moieties found on the polyalkylene oxide backbone are generally prepared by either converting a hydroxyl group on the polyalkylene oxide backbone to the ethylenically unsaturated moiety or by reacting the alkylene oxide monomer with an ethyleneically unsaturated moiety containing a hydroxyl group under polymerization conditions. Additional methods are well known in the art.

The term "a glycidyl residue" refers to derivatives of glycerol ($HOCH_2CHOHCH_2OH$) which have a polyalkylene oxide $-(CH_2CHR^2O)_nH$ moiety attached to at least one, and preferably all three, of the oxygen atoms of the hydroxyl groups (by replacement of the proton of the hydroxyl group) where $R^2$ and n are as defined above. In turn, each of the hydroxyl groups found on these derivatives are then converted to an ethylenically unsaturated moiety (e.g., a substituent of the formula

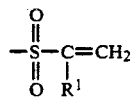

where $R^1$ is as defined above). Additionally, included within the term "glycidyl" are glycidyl moieties wherein one or more of the carbon atoms of the glycidyl moiety are substituted with an alkyl group of from 1 to 4 carbon atoms.

The term "electrolytic cell" refers to a composite containing an anode, a cathode, and an ion-conducting electrolyte interposed therebetween.

The anode is typically comprised of a compatible anodic material which is any material which functions as an anode in a solid electrolytic cell. Such compatible anodic materials are well known in the art and include, by way of example, lithium, lithium alloys, such as alloys of lithium with aluminum, mercury, nickel, zinc, and the like, and intercalation based anodes such as carbon, $WO_3$, and the like.

The cathode is typically comprised of a compatible cathodic material (i.e., insertion compounds) which is any material which functions as a positive pole in a solid electrolytic cell. Such compatible cathodic materials are well known in the art and include, by way of example, manganese dioxide, molybdenum trioxide, vanadium pentaoxide, sulfides of titanium and niobium, chromium oxide, copper oxide, $V_6O_{13}$ and the like. The particular compatible cathodic material employed is not critical.

In one preferred embodiment, the compatible cathodic material is mixed with an electroconductive material including, by way of example, graphite, powdered carbon, powdered nickel, metal particles, conductive polymers (i.e., characterized by a conjugated network of double bonds like polypyrrole and polyacetylene), and the like, and a binder such as poly(tetrafluoroethylene) to form under pressure a positive cathodic plate.

In another preferred embodiment, the cathode is prepared from a cathode paste which comprises from about 35 to 65 weight percent of a compatible cathodic material; from about 1 to 20 weight percent of an electroconductive agent; from about 0 to 20 weight percent of polyethylene oxide having a number average molecular weight of at least 100,000; from about 10 to 50 weight percent of the electrolyte solvent; and from at least about 5 weight percent to 30 weight percent of a solid polymeric matrix derived from the monomer of Formula I above. (All weight percents are based on the total weight of the cathode.)

The cathode paste is typically spread onto a suitable support such as a current collector and then cured by conventional methods to provide for a solid positive cathodic plate. The cathode (excluding the support) generally has a thickness of about 20 to about 150 microns.

Current collectors are well known in the art some of which are commercially available. A particularly preferred current collector for the cathode is a roughened nickel (electrolytically deposited nickel) on nickel current collector (available as CF18/NiT from Fukuda Metal Foil & Powder Company, Ltd., Kyoto, Japan). The current collectors are preferably attached to the surface of the cathode not facing the electrolyte but can also be attached to the anode. When the current collector is attached to the cathode, the cathode is interposed between the electrolyte and the current collector.

In still another preferred embodiment, the electrolyte solvent and the cathode solvent are identical.

Methodology

Methods for preparing solid electrolytes are well known in the art. This invention, however, utilizes a particular monomer in the preparation of solid polymeric matrix used in the solid electrolytes which monomer is represented by Formula I:

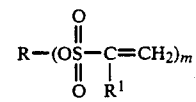

where R, $R^1$, and m are as defined above.

The monomers of Formula I above are readily prepared as shown in reaction (1) below:

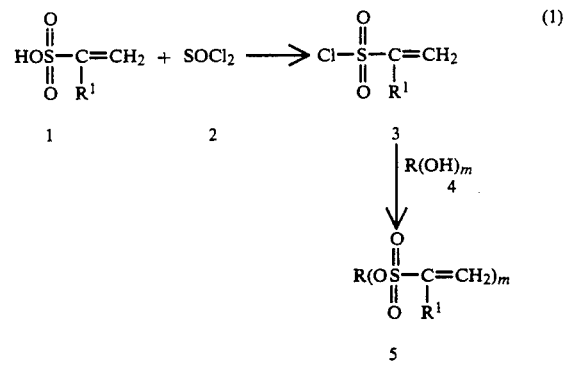

Specifically, in reaction (1), the vinylsulfonic acid (compound 1) is first converted to the acid chloride by contacting the acid with at least an equimolar amount and preferably an excess amount of thionyl chloride (compound 2). This reaction is conducted either neat or in an inert anhydrous solvent such as methylene chloride, chloroform, ethyl acetate, toluene, and the like. The reaction is generally conducted under an inert anhydrous atmosphere at from about 0° C. to about 30° C. The reaction is generally complete in about 0.5 to 3 hours.

The resulting acid chloride (compound 3) is then reacted with $R(OH)_m$ (compound 4). In general, at least m moles and preferably about $1.1 \times m$ moles of acid chloride is used per mole of R(OH)$_m$ under conditions such that all of the hydroxyl groups on compound 4 are converted to

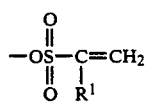

groups. Suitable reaction conditions include reaction temperatures of from about 0° to about 50° C. and reaction times of from 0.5 to 6 hours. The reaction is generally conducted in an inert, anhydrous solvent such as methylene chloride, dimethylformamide, ethyl acetate and the like. A tertiary amine such as triethylamine can be added to the solvent to scavenge the acid generated by the reaction or, alternatively, a solvent such as pyridine can be employed. The product (compound 5) is then recovered by conventional techniques such as column chromatography, high performance liquid chromatography, distillation and the like. However, care should be taken during the recovery procedure (especially if distillation is employed) to prevent polymerization of the monomer.

The free acid (compound 1) is readily prepared from the acid salt by contacting with an aqueous acidic solution (e.g., 1N HCl). Some of the acid salts are commercially available (e.g., $CH_2=CHSO_3^-Na^+$) and others can be prepared by conventional procedures well known in the art. For example, the known $BrCH_2CH(CH_3)SH$ compound [Journal of Organic Chemistry, Vol. 33, pp. 2895-2902 (1968)] can be converted to $BrCH_2CH(CH_3)SO_3H$ by reaction first with $Pb(NO_3)_2$ and then with $HNO_3$ as per Cram & Hammond, "Organic Chemistry, p.441, McGraw-Hill, New York, N.Y., (1959). Dehydrobromination under alkaline conditions (sodium methoxide/methanol) provides for the sodium salt of the $CH_2=C(CH_3)SO_3H$ acid.

The solid, solvent-containing electrolyte is then preferably prepared by combining a compound of Formula I or a mixture of compounds of Formula I with an inorganic ion salt and the electrolyte solvent. The resulting composition is then uniformly coated onto a suitable substrate (e.g., aluminum foil, a glass plate, a lithium anode, a cathode, etc.) by means of a roller, a doctor blade, a bar coater, a silk screen or spinner to obtain a film of this composition or its solution. In some cases, it may be necessary to heat the composition so as to provide for a coatable material.

Preferably, the amount of material coated onto the substrate is an amount sufficient so that after curing, the resulting solid, solvent-containing electrolyte has a thickness of no more than about 250 microns (μm). Preferably, the solid, solvent-containing electrolyte has a thickness of from about 25 to about 250 microns, more preferably from about 50 to about 150 microns, and even more preferably from about 80–100 microns.

The electrolyte composition tppically comprises from about 5 to about 25 weight percent of an inorganic ion salt based on the total weight of the electrolyte; preferably, from about 10 to 20 weight percent; and even more preferably about 15 weight percent.

The electrolyte composition typically comprises from about 40 to about 80 weight percent solvent based on the total weight of the electrolyte; preferably from about 60 to about 80 weight percent; and even more preferably about 70 weight percent.

The solid electrolyte composition typically comprises from about 5 to about 30 weight percent of the polymer derived from a compound of Formula I based on the total weight of the electrolyte; preferably from about 10 to about 20 weight percent; and even more preferably about 17 weight percent.

In a preferred embodiment, the electrolyte composition further comprises a small amount of a film forming agent. Suitable film forming agents are well known in the art and include, by way of example, polypropylene oxide, polyethylene oxide, copolymers thereof, and the like, having a numbered average molecular weight of at least about 100,000. Preferably, the film forming agent is employed in an amount of about 1 to about 10 weight percent and more preferably at about 2.5 weight percent based on the total weight of the electrolyte composition.

The composition is cured by conventional methods to form a solid film. For example, suitable curing methods include heating, irradiation with UV radiation, irradiation with electron beams (EB), etc. When the composition is cured by heating or UV radiation, the composition preferably contains an initiator. For example, when curing is by heating, the initiator is typically a peroxide such as benzoyl peroxide, methyl ethyl ketone peroxide, t-butyl peroxypyvarate, diisopropyl peroxycarbonate, and the like). When curing is by UV radiation, the initiator is typically benzophenone, Darocur 1173 (Ciba Geigy, Ardlesy, N.Y.), and the like.

The initiator is generally employed in an amount sufficient to catalyze the polymerization reaction. Preferably, the initiator is employed at up to about 1 weight percent based on the weight of the solid matrix forming monomer.

When curing is by EB treatment, an initiator is not required.

Without being limited to any theory, it is believed that the monomers of this invention provide for enhanced rates of polymerization as compared to other similar monomers (e.g., acryloyl-derivatized polyalkylene oxide) and, accordingly, provide for more facile polymerization because the electron withdrawing effects of the sulfonate substituent activate the ethylenic group to polymerization. In any event, the monomers of Formula I are readily polymerized under suitable polymerization conditions.

In an alternative embodiment, the solid polymeric matrix (e.g., formed by polymerization of a solid matrix forming monomer) can be dissolved into a suitable volatile solvent and the requisite amounts of the inorganic ion salt and electrolyte solvent are then added. The mixture is then applied onto a suitable substrate (e.g., the surface of the cathode opposite to the current collector) in the manner set forth above and the volatile solvent removed by conventional techniques to provide for a solid electrolyte. Suitable volatile solvents preferably have a boiling point of less than 85° C. and more preferably between about 45° and 85° C. Particularly preferred volatile solvents are aprotic solvents. Examples of suitable volatile solvents include acetonitrile, tetrahydrofuran and the like. However, acetonitrile is not preferred if it is to contact the anode.

In either case, the resulting solid electrolyte is a homogeneous, single phase material which is maintained upon curing, and which does not readily separate upon cooling to temperatures below room temperature. See, for example, U.S. Pat. No. 4,925,751 which is incorporated herein by reference in its entirety.

Additionally, it is desirable to avoid the use of any protic materials which will be incorporated into the battery. For example, most of the protic inhibitors for preventing premature monomer polymerization (e.g., protic inhibitors found in di- and triacrylate monomers) employed with the monomers are preferably removed prior to formation of the solid matrix (e.g., the cathode and/or electrolyte) by contact with a inhibitor remover such as Inhibitor Remover available as product number 31,133-2 from Aldrich Chemical, Milwaukee, Wis. Such processes generally will lower the inhibitor concentration to less than about 50 ppm.

In a preferred embodiment, the process of forming an electrolytic cell comprises the steps of coating the surface of a cathode with a composition comprising requisite amounts of a compound of Formula I or a mixture of compounds of Formula I, an inorganic ion salt and the electrolyte solvent. The composition is then cured to provide for a solid electrolyte on the cathodic surface. The anode (e.g., a lithium foil) is then laminated to this composite product in such a way that the solid electrolyte is interposed between the lithium foil and the cathodic material.

This process can be reversed so that the surface of a anode is coated with a composition comprising requisite amounts of a compound of Formula I or a mixture of compounds of Formula I, an inorganic ion salt and the electrolyte solvent. The composition is then cured to provide for a solid electrolyte on the anodic surface. The cathode is then laminated to this composite product in such a way that the solid electrolyte is interposed between the lithium foil and the cathodic material.

Methods for preparing solid electrolytes and electrolytic cells are also set forth in U.S. Pat. Nos. 4,830,939 and 4,925,751 which are incorporated herein by reference in their entirety.

The following examples are offered to illustrate the present invention and should not be construed in any way as limiting its scope.

EXAMPLES

Example 1

Preparation of a Divinyl Sulfonate Derivative of Decaethylene Glycol

A divinyl sulfonate derivative of decaethylene glycol [H(OCH$_2$CH$_2$)$_{10}$OH] was prepared as follows:

Approximately, 100 g of vinyl sulfonate, sodium salt (available from Aldrich Chemical Company, Milwaukee, Wis.) are converted to its free acid by addition to an aqueous solution of 1N HCl. After stirring at room temperature for 1 hour, the free acid is then recovered by conventional means, e.g., extraction with ethyl acetate, drying with anhydrous magnesium sulfate.

The vinyl sulfonic acid is then converted to its acid chloride by reaction with approximately 1.1 equivalents of thionyl chloride at 10° C. with stirring for 30 minutes under a nitrogen atmosphere. The resulting product is then reacted with sufficient polyethylene glycol [HO(CH$_2$CH$_2$O)$_n$H—MW about 600 (n=~10) which is obtained from Aldrich Chemical Company, Milwaukee, Wis.] so as to provide approximately 1.1 equivalents of the vinyl sulfonic acid chloride per hydroxyl group. The reaction is conducted in ethyl acetate containing sufficient triethylamine to scavenge the acid generated. The reaction temperature is generally between about 10°-20° C. and the reaction is allowed to continue until complete (as determined by TLC). At this time, the reaction mixture is washed with water, aqueous sodium bicarbonate and water. The organic phase is then dried over anhydrous magnesium sulfate, filtered and the resulting product purified via column chromatography to provide for a vinyl sulfonate polyalkylene oxide of the formula:

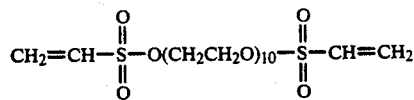

Example 2

Preparation of a Solid Battery Containing a Solid Electrolyte Having a Solid Polymeric Matrix Derived from the Vinyl Sulfonate Polyalkylene Oxide of Example 1

A solid battery is prepared by first preparing a cathodic paste which is spread onto a substrate (e.g., a current collector) and then is cured to provide for the cathode. An electrolyte composition is then placed onto the cathode surface and is cured to provide for the solid electrolyte. Then, the anode is laminated onto the solid electrolyte to provide for a solid battery. The specifics of this construction are as follows:

A. The Cathode

The cathode is prepared from a cathodic paste which, in turn, is prepared from a cathode powder as follows:

i. Cathode Powder

The cathode powder is prepared by combining 90.44 weight percent V$_6$O$_{13}$ [prepared by heating ammonium metavanadate (NH$_4$+VO$_3$−) at 450° C. for 16 hours under N$_2$ flow] and 9.56 weight percent of carbon (from Chevron Chemical Company, San Ramon, Calif. under the tradename of Shawinigan Black ™). About 100 grams of the resulting mixture is placed into a grinding machine (Attritor Model S-1 purchased from Union Process, Akron, Ohio) and ground for 30 minutes. Afterwards, the resulting mixture is dried at about 260° C. for 16 hours to provide a cathode powder having about 84.45 weight percent V$_6$O$_{13}$.

ii. Cathode Paste

A cathode paste is prepared by combining sufficient cathode powder to provide for a final product having 45 weight percent V$_6$O$_{13}$.

Specifically, about 28.71 grams of unground carbon (from Chevron Chemical Company, San Ramon, Calif. under the tradename of Shawinigan Black ™) is combined in a glove box [under dry (<10 ppm H$_2$O) argon at ambient temperature and pressure] with about 57.2 grams of the 1:1 mixture of ethylene carbonate/triglyme and the resulting composite is mixed under dry argon and at ambient temperature and pressure on a double planetary mixer (Ross #2 mixer available from Charles Ross & Sons, Company, Hauppag, N.Y.) at about 20 rpms until a paste is formed.

About 248.77 grams of a cathode powder prepared in a manner similar to that described above is added to the mixer along with an additional 57.2 grams of the 1:1 mixture of ethylene carbonate/triglyme and the resulting composite is mixed under dry argon and at ambient temperature and pressure on a double planetary mixer at about 20 rpms until a dry paste is formed.

About 5 grams of polyethylene oxide (number average molecular weight about 600,000 available as Polyox WSR-205 from Union Carbide Chemicals and Plastics, Danbury, Conn.), about 42.9 grams of polyethylene glycol diacrylate (molecular weight about 400 available as SR-344 from Sartomer Company, Inc., Exton, Pa.), and about 7.6 grams of ethoxylated trimethylpropane triacylate (TMPEOTA) (molecular weight about 450 available as SR-454 from Sartomer Company, Inc., Exton, Pa.) are added to about 57.2 grams of a 1:1 mixture of triglyme/ethylene carbonate and this mixture is added to the mixer.

The resulting slurry in the mixer is heated at about 65° C. while mixing for 2 hours at 60 rpms to provide for the cathodic paste which has the following approximate weight percent of components:

| | |
|---|---|
| $V_6O_{13}$ | 45 weight percent |
| Carbon | 10 weight percent |
| ethylene carbonate/triglyme | 34 weight percent |
| polyethylene oxide | 1 weight percent |
| polyethylene glycol diacrylate[1] | 8.5 weight percent |
| ethoxylated trimethylpropane triacrylate[1] | 1.5 weight percent |

[1]The inhibitor in both the polyethylene glycol diacrylate and ethoxylated trimethylpropane triacrylate is removed by contacting each of these compounds with an Inhibitor Remover available as Product No. 31,133-2 from Aldrich Chemical, Milwaukee, Wisconsin. In each case, the concentration of inhibitor is reduced to less than 50 ppm.

In an alternative embodiment, the requisite amounts of all of the cathodic materials other than the cathode powder can be combined to form a first mixture and this first mixture is combined with the cathode powder to form a second mixture. This second mixture is then thoroughly mixed to provide for the cathode paste.

The cathode paste prepared as above is placed onto a sheet [about 1 mil (~25 μm) thick by 10 cm wide] of a roughened nickel on nickel current collector (available as CF18/NiT from Fukuda Metal Foil & Powder Company, Ltd., Kyoto, Japan). A Mylar cover sheet is then placed over the paste and the paste is spread to thickness of about 90 microns (μm) with a conventional plate and roller system and is cured by continuously passing the sheet through an electron beam apparatus (Electrocurtain, Energy Science Inc., Wolburn, Mass.) at a voltage of about 1.75 kV and a current of about 1.0 mA and at a rate of about 1 cm/sec. After curing, the Mylar sheet is removed to provide for a solid cathode laminated to a nickel on nickel current collector.

B. Electrolyte

The electrolyte is prepared by first combining about 137.48 grams of a 1:1 mixture of ethylene carbonate/triglyme and about 34.26 grams of the compound prepared in Example 1 above. If necessary, the resulting solution is passed through a column of Inhibitor Remover (available as Product No. 31,133-2 from Aldrich Chemical, Milwaukee, Wis.) and then through a column of 4-5 Å molecular sieves to remove water.

This solution is then combined with about 5.02 grams of polyethylene oxide (number average molecular weight about 600,000 available as Polyox WSR-205 from Union Carbide Chemicals and Plastics, Danbury, Conn.). Once the polyethylene oxide is dispersed, about 23.24 grams of $LiAsF_6$ (available from FMC Corporation Lithium Division, Bessemer City, N.C., as Lectrosalt ™) is added while stirring with a laboratory mixer (Yamato Model LR41B, available from Fisher Scientific, Santa Clara, Calif.). Alternatively, the salt can be added before the polyoxyethylene oxide and then, after dissolution of the salt, the polyoxyethylene oxide can be added and stirred until dispersed.

The resulting 200 gram mixture contains the following weight percent of components:

| | |
|---|---|
| ethylene carbonate | 34.37 weight percent |
| triglyme | 34.37 weight percent |
| polyethylene oxide | 2.51 weight percent |
| vinyl sulfonate (Ex. 1) | 17.13 weight percent |
| $LiAsF_6$ | 11.62 weight percent |

The mixture is then thoroughly mixed with the same laboratory mixer at heating until a temperature of about 85° C. is reached and then cooled to ambient temperature over at least a 2 hour period while stirring is maintained. The mixture is then placed into a vacuum (about 0.1 torr) for about 30 minutes.

Afterwards, the electrolyte mixture is then coated by a conventional knife blade to a thickness of about 50 μm onto the surface of the cathode sheet prepared as above (on the side opposite that of the current collector) but without the Mylar covering. The electrolyte is then cured by continuously passing the sheet through an electron beam apparatus (Electrocurtain, Energy Science Inc., Wolburn, Mass.) at a voltage of about 1.75 kV, a current of about 1.0 mA, and a rate of about 1 cm/sec. After curing, a composite is recovered which contained a solid electrolyte laminated to a solid cathode which, in turn, is laminated to a nickel on nickel current collector.

C. Anode

The anode comprises a sheet of lithium foil (about 76 μm thick) which is commercially available from FMC Corporation Lithium Division, Bessemer City, N.C.

D. The Solid Battery

A sheet comprising a solid battery is prepared by laminating the lithium foil anode to the surface of the electrolyte in the sheet produced in step C above. Lamination is accomplished by minimal pressure.

By following the procedure set forth in Examples 1 and 2 above, other vinyl sulfonate polyalkylene oxides can be substituted in place of

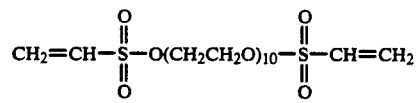

Such other vinyl sulfonates include those where n is an integer from 2 to 50, where $R_1$ is methyl, ethyl, n-propyl, etc., and the like.

What is claimed is:

1. A compound of the formula I:

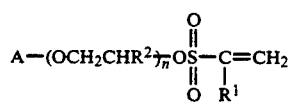

where $R^1$ is selected from the group consisting of hydrogen and alkyl of from 1 to 6 carbon atoms; $R^2$ is selected from the group consisting of hydrogen and an alkyl group of from 1 to 3 carbon atoms;
A is selected from the group consisting of a hydrocarbyl group of from 1 to 30 carbon atoms and a compatible ethylenically unsaturated moiety of from 2 to 6 carbon atoms; and n is an integer from about 2 to 50.

2. A compound according to claim 1 wherein $R^1$ is hydrogen.

3. A compound according to claim 2 above wherein n is an integer from about 3 to about 30.

4. A compound according to claim 3 above wherein n is an integer of about 10.

5. A compound according to claim 1 wherein A is

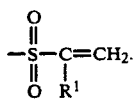

6. A single phase, solid, solvent-containing electrolyte which comprises:
a solid polymeric matrix;
an inorganic ion salt; and
a solvent;
wherein said solid polymeric matrix is obtained by polymerizing an organic monomer represented by Formula I:

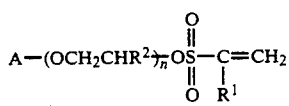

wherein $R^1$ is selected from the group consisting of hydrogen and alkyl of from 1 to 6 carbon atoms; $R^2$ is selected from the group consisting of hydrogen and an alkyl group of from 1 to 3 carbon atoms; A is selected from the group consisting of a hydrocarbyl group of from 1 to 30 carbon atoms and a compatible ethylenically unsaturated moiety of from 2 to 6 carbon atoms; and n is an integer from about 2 to 50.

7. A single phase, solid, solvent-containing electrolyte according to claim 6 wherein $R^1$ is hydrogen.

8. A single phase, solid, solvent-containing electrolyte according to claim 7 above wherein n is an integer of from about 3 to about 30.

9. A single phase, solid, solvent-containing electrolyte according to claim 7 above wherein n is an integer of about 10.

10. A single phase, solid, solvent-containing electrolyte according to claim 6 wherein A is

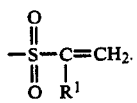

11. An electrolytic cell which comprises:
an anode comprising a compatible anodic material;
a cathode comprising a compatible cathodic material; and
interposed therebetween a single phase, solid, solvent-containing electrolyte which comprises:
a solid polymeric matrix;
an inorganic ion salt; and
a solvent wherein said solid polymeric matrix is obtained by polymerizing an organic monomer represented by Formula I:

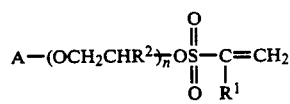

where $R^1$ is selected from the group consisting of hydrogen and alkyl of from 1 to 6 carbon atoms; $R^2$ is selected from the group consisting of hydrogen and an alkyl group of from 1 to 3 carbon atoms; A is selected from the group consisting of a hydrocarbyl group of from 1 to 30 carbon atoms and a compatible ethylenically unsaturated moiety of from 2 to 6 carbon atoms; and n is an integer from about 2 to 50.

12. An electrolytic cell according to claim 11 wherein $R^1$ is hydrogen.

13. An electrolytic cell according to claim 12 above wherein n is an integer of from about 3 to about 30.

14. An electrolytic cell according to claim 12 above wherein n is about 10.

15. An electrolytic cell according to claim 11 wherein A is

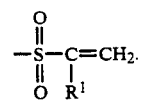

16. A compound of the formula:

$$\begin{array}{c} CH_2-R^3 \\ | \\ CH-R^4 \\ | \\ CH_2-R^5 \end{array}$$

wherein $R^3$, $R^4$, and $R^5$ are selected from the group consisting of:

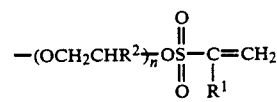

and

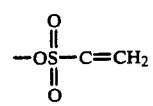

with the proviso that at least one of $R^3$, $R^4$ or $R^5$ is the group

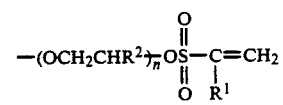

and further wherein $R^1$ is selected from the group consisting of hydrogen and alkyl of from 1 to 6 carbon atoms; $R^2$ is selected from the group consisting of hydrogen and an alkyl group of from 1 to 3 carbon atoms; and n is an integer from about 2 to about 50.

17. A compound according to claim 16 above wherein $R^1$ is hydrogen.

18. A compound according to claim 17 above wherein n is an integer from about 3 to about 30.

19. A single phase, solid, solvent-containing electrolyte which comprises:

a solid polymeric matrix;

an inorganic ion salt; and a solvent;

wherein said solid polymeric matrix is obtained by polymerizing an organic monomer represented by the formula:

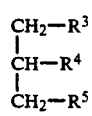

wherein $R^3$, $R^4$, and $R^5$ are selected from the group consisting of:

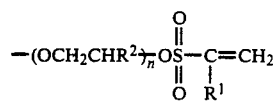

and

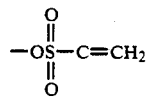

with the proviso that at least one of $R^3$, $R^4$ or $R^5$ is the group

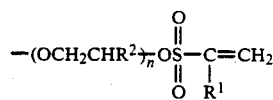

and further wherein $R^1$ is selected from the group consisting of hydrogen and alkyl of from 1 to 6 carbon atoms; $R^2$ is selected from the group consisting of hydrogen and an alkyl group of from 1 to 3 carbon atoms; and n is an integer from about 2 to about 50.

20. A single phase, solid, solvent-containing electrolyte according to claim 19 above wherein $R^1$ is hydrogen.

21. A single phase, solid, solvent-containing electrolyte according to claim 20 above wherein n is an integer of from about 3 to about 30.

22. An electrolytic cell which comprises:

an anode comprising a compatible anodic material;

a cathode comprising a compatible cathodic material; and interposed therebetween a single phase, solid, solvent-containing electrolyte which comprises:

a solid polymeric matrix;

an inorganic ion salt; and a solvent wherein said solid polymeric matrix is obtained by polymerizing an organic monomer represented by the formula:

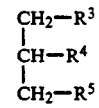

wherein $R^3$, $R^4$, and $R^5$ are selected from the group consisting of:

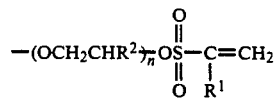

and

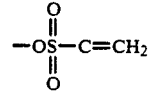

with the proviso that at least one of $R^3$, $R^4$ or $R^5$ is the group

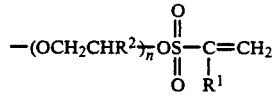

and further wherein $R^1$ is selected from the group consisting of hydrogen and alkyl of from 1 to 6 carbon atoms; $R^2$ is selected from the group consisting of hydrogen and an alkyl group of from 1 to 3 carbon atoms; and n is an integer from about 2 to about 50.

23. An electrolytic cell according to claim 22 above wherein $R^1$ is hydrogen.

24. An electrolytic cell according to claim 23 above wherein n is an integer of from about 3 to about 30.

* * * * *